United States Patent [19]
Kraemer

[11] Patent Number: 5,427,089
[45] Date of Patent: Jun. 27, 1995

[54] VALVED AUXILIARY DEVICE FOR USE WITH AEROSOL CONTAINER

[75] Inventor: Richard Kraemer, Bern, Switzerland

[73] Assignee: Glaxo Group Limited, Greenford, United Kingdom

[21] Appl. No.: 117,988

[22] Filed: Sep. 8, 1993

Related U.S. Application Data

[63] Continuation of Ser. No. 995,337, Dec. 22, 1992, abandoned, which is a continuation of Ser. No. 887,559, May 18, 1992, abandoned, which is a continuation of Ser. No. 743,910, Aug. 12, 1991, abandoned, which is a continuation of Ser. No. 655,732, Feb. 14, 1991, abandoned, which is a continuation of Ser. No. 509,961, Apr. 16, 1990, abandoned.

[30] Foreign Application Priority Data

Apr. 17, 1989 [GB] United Kingdom ............... 8908647

[51] Int. Cl.⁶ ............... A61M 11/00; A61M 16/00; A62B 18/02
[52] U.S. Cl. .................. 128/200.23; 128/200.14; 128/203.29
[58] Field of Search ........... 128/200.14, 200.23, 128/203.12, 203.15, 203.29

[56] References Cited

U.S. PATENT DOCUMENTS

| | | | |
|---|---|---|---|
| 3,236,458 | 2/1966 | Ramis | 128/200.23 |
| 4,174,712 | 11/1979 | Morén et al. | 128/200.14 |
| 4,470,412 | 9/1984 | Nowacki et al. | 128/200.23 |
| 4,534,343 | 8/1985 | Nowacki | 128/200.23 |
| 4,641,644 | 2/1987 | Andersson et al. | 128/200.23 |
| 4,796,614 | 1/1989 | Nowacki et al. | 128/200.14 |
| 4,809,692 | 3/1989 | Nowacki et al. | 128/206.24 |
| 4,926,852 | 5/1990 | Boltan et al. | 128/200.23 |
| 4,953,545 | 9/1990 | McCarty | 128/200.23 |
| 5,074,294 | 12/1991 | Chiesi | 128/200.14 |

FOREIGN PATENT DOCUMENTS

| | | | |
|---|---|---|---|
| 0009667 | 4/1980 | European Pat. Off. | |
| 0015247 | 9/1980 | European Pat. Off. | |
| 0074937 | 3/1983 | European Pat. Off. | |
| 0134847 | 3/1985 | European Pat. Off. | |
| 251443 | 1/1988 | European Pat. Off. | |
| 0347779 | 12/1989 | European Pat. Off. | 128/200.14 |
| 446919 | 5/1936 | United Kingdom | |
| 975754 | 11/1964 | United Kingdom | |
| 1017032 | 1/1966 | United Kingdom | |
| 1109218 | 4/1968 | United Kingdom | |
| 2110543 | 6/1983 | United Kingdom | |
| 2137886 | 10/1984 | United Kingdom | |
| 2182249 | 5/1987 | United Kingdom | |
| 1544440 | 2/1990 | U.S.S.R. | 128/200.23 |
| 8303976 | 11/1983 | WIPO | |
| 8802267 | 4/1988 | WIPO | 128/203.15 |
| 8803419 | 5/1988 | WIPO | |
| 9100117 | 1/1991 | WIPO | 128/200.23 |

OTHER PUBLICATIONS

A technological advance in the treatment of asthma; G. Beaumont; Medical News 16/23 Dec. 1982 14 (48), 28.
Terbutaline Nebuhaler; I. James; Geriatric Medicine, Dec. 1982, 22.

(List continued on next page.)

*Primary Examiner*—Kimberly L. Asher
*Attorney, Agent, or Firm*—Darby & Darby

[57] ABSTRACT

An auxiliary device is provided for use with a metered-dose aerosol device. The auxiliary device comprises a chamber having an inlet adapted to receive the metered-dose aerosol device, and an outlet. A mask adapted to communicate with the nose and/or mouth of an infant or young child communicates with the chamber outlet via a first valve which permits the infant or young child to inhale aerosol-carrying air from the chamber, and communicates with atmosphere via a second valve permitting exhalation therethrough. The distance between the chamber inlet and the chamber outlet is such that the mass percentage of aerosol particles having a diameter of from 1.0 microns to 5.0 microns is substantially a maximum at the chamber outlet, and the volume of the chamber is from 200–500 ml.

8 Claims, 2 Drawing Sheets

OTHER PUBLICATIONS

The effect of an aerochamber on bronchodilator response to a metereddose inhaler; P. Lawford; D. McKenzie, D. Alston; Practitioner 1982, 226, 2093.

Spacer device with face mask attachment for giving brochodilators to infants with asthma; C. O'Callaghen, A. D. Milner; A. D. Swarbrick; Brit Medical Journal 1989, 298, 160.

Delivery of albuterol aerosol by Inhal-Aid to your children; B. Chang; R. M. Sly, D. Eby, H. B. Middleton; Journal of Allergy and Clinic Immunology 1985, 75, 159.

The Aerochamber: A new demand-inhalation device for delivery of aerosolized drugs; D. Corr, M. Dolovich, D. McCormack, R. Ruffin, G. Obminski, M. Newhouse; Amer. Rev. Resp. Dis. 1989, 121 Suppl. 4, 123.

Pressurized Aerosols inhaled through extension devices; I. C. Aghurst, Journal of Aerosol Sciences, vol. 14, No. 1, 1983 69.

Design and characteristics of a portable breath actuated, particle size selective medical aerosol inhaler; D. Corr, M. Dolovich, D. McCormack, R. Ruffin, G. Obminiski, M. Newhouse; Journal of Aerosol Sciences, vol. 13, No. 1, 1982, pp. 1-7.

Evaluation of Inhalation Airs of Metered Dose Inhalers in Asthmatic Children, Haesoon Lee, Hugh E. Evans, Chest Mar. 1967, pp. 366-369; Oropharyngeal Deposition and Delivery Aspects of Metered-Dose Inhaler Aerosols, Chong S. Kim, Mungen A. Eldridge and Marvin A. Sackner, Am. Rev. Respir. Dis. 1987, pp. 157-164.

Spacer device with face mask attachment for giving bronchodilators to infants with asthma, C. O'Callaghan, A. D. Milner, A. Swarbrick, BMJ, 21 Jna. 1989, pp. 160-161.

Reliable Salbutamol Administration in 6-to 36-Month-Old Children by Means of a Metered Dose Inhaler and Aerochamber With Mask, W. T. Conner, M. B. Dolovich, R. A. Frame and M. T. Newhouse, Pediatric Pulmonology, 1989, pp. 263-267.

Bronchodilator Effect of Fenoterol and Ipratropium Bromide in Infants with Acute Wheezing, J. Mallol, Luis Barrueto, Guido Girardi and O. Toro, Pediatric Pulmonary, 1987, pp. 352-356.

Clinical Evaluation of a Simple Demand Inhalation MDI Aerosol Delivery Device, M. Dolovich, R. Ruffin, D. Cort and M. T. Newhouse, Chest, Jul. 1983, pp. 36-41 Assessment of a new device for delivering aerosol drugs to asthmatic children, I. G. C. Hodges, A. D. Milner and G. M. Stokes, Arch. of Dis. in Children, 1981, pp. 787-800.

Response to Bronchodilator Drug Administration by a New Reservoir Aerosol Delivery System and a Review of Other Auxiliary Delivery Systems, M. J. Tobin, G. Jenouri, I. Danta, C. Kim, H. Watson and M. A. Sackner, Anr. Ref. Respir. Dir. 1982, pp. 670-675.

Bronchodilatation with a Metered-Dose Inhaler Plus an Extension, Using Tidal Breathing vs. Jet Nebulization, A. Gervais and P. Begin, Chest, Nov. 1967, pp. 822-824; Optimal inhalation technique with terbutaline Turbuhaler, O. R. Hansen, S. Pedersen, Eur. Respir. J. 1989, pp. 637-639.

New Inhalation Devices, G. K. Crompton, Eur. Respir. J., 1988, pp. 679-680; A dose-response study of inhaled terbutaline administered via Nebuhaler or nebuliser to asthmatic children; M. Blackhall and S. O'Donnell, Eur. J. Respir. J., 1988, pp. 679-680.

Particle size study of nine metered dose inhalers, and their deposition probabilities in the airways, A. Bouchikhi, M. H. Mecquemin, J. Bignon, M. Roy and T. Teillac, Eur. Respir. J. 1988, pp. 547-552.

Deposition and clinical efficacy of terbutaline sulphate from Turbuhaler, a new multi-dose powder inhaler, S. P. Newman, F. Moren, E. Trofast, N. Talaee and S. W. Clarke, Eur. Respir. J. 1989, pp. 247-252.

Effect of InspirEase on the Deposition of Meterd-Dose Aerosols in the Human Respiratory Tract, S. P. Newman, G. Woodman, S. W. Clarke and M. A. Sackner, Chest, Apr. 1966, pp. 551-556.

Response to Bronchodilator Drug Administration by a New Reservoir Aerosol Delivery System and a Review of Other Auxiliary Delivery Systems, M. J. Tobin, G. Jenouri, I. Danta, C. Kim, H. Watson and M. A. Sackner, Am. Rev. Respir. Dis. 1982, pp. 670-675.

Size Aspect of Metered-Dose Inhaler Aerosols, C. S. Kim, D. Trujillo and M. A. Sackner, Am. Ref. Respir. Dis. 1985, pp. 137-142.

Principles of Aerosol Therapy, M. T. Newhouse, Chest, Jul. 1982 Supplement, pp. 395-415.

Spacer Devices User with Metered-Dose Inhalers, Breakthrough or Gimmick?, Peter Konig, Chest 1985, pp. 276-284.

OTHER PUBLICATIONS

Aerochamber Advertisement.

Aerochamber Advertisement, Dec. 1985.

Size Distributions of Metered-Dose Inhaler Aerosols; E. Russi, L. Pedrocchi, K. Marguardty, Eur. J. Resp. Dis. 1988(2) 211S.

Charakterisierung Therapeutischer Dosier-Acrosole; H. Blocklinger, L. Pedrucchi, N. Marquard, E. Russi; Institute fur Verflhrens pp. 19-20.

Use of a Special Inhaler Attachment In Asthmatic Children; R. Ellul-Micallef, et, al.; Thorax (1980); 35:620-623.

*Aerosol Age* "Aerosolized Drug Delivery Accessories"; A. J. Cutie, et al; Mar., 1984 pp. 24-25, 47.

Evaluation of Bronchodilation From Aerosol Beta Agonists Delivered By The Inhal-Aid Device To Young Children; W. Huntley, et al; Journal of Asthma (1984); 21(4), 265-270.

Metered Dose Inhaler; Annals of Internal Medicine (1984); 100(4), I-19.

Inhalation Device and Aerosol Therapy; C. Barley; On Continuing Practice (1989) 16(1), 30-39.

Aerosol Bag For Administration Of Bronchodilators to Young Asthmatic Children; H. Lee, et al; Pediatrics (1984); 73(2), 230-232.

New Method of Beclomethasone Aerosol Administration To Children Under 4 Years Of Age (*CMA Journal* Dec. 3, 1977, vol. 117).

The Blo-Bag, A Disposable Spacer (*Postgraduate Medical Journal*, 1984).

Chamber Assisted Inhalant Treatment (CAIR) (*Annals of Allergy*, 1983).

Addition of a Spacer Device As An Alternative In Treatment With A Metered Dose Inhaler; H. Dirksen; Eur. J. Resp. Dis. (1983); 64 [Suppl.] 30:42-47.

Aerosol-In-Bag Administrations of Inhaled Bronchodilators; Feisal A. El-Kassimi; Eur. J. Resp. Dis. (1987); 70:234-238.

Fenoterol Plus Ipratropium (Duovent) Aerosol Therapy Delivered By A Tube Spacer; Ashley Woodcock et al.; Pharmatherapeutica (1984) 50:166-170.

Assessment Of A New Device (Aerochamber) For Use With Aerosol Drugs In Asthmatic Children; D. Gurwitz et al; Annals of Allercy (1983) 50:166-170.

Aerosol Treatment of Bronchoconstriction In Children With Or Without A Tube Spacer; S. Pederson; New Eng. J. Medicine (1983); 308(22), 2 Jun., 1328-30.

Spacer Devices Used With Metered-Dose Inhalers—Breakthrough or Gimmick?; P. Konig; Chest (1985); 88(2):276-284.

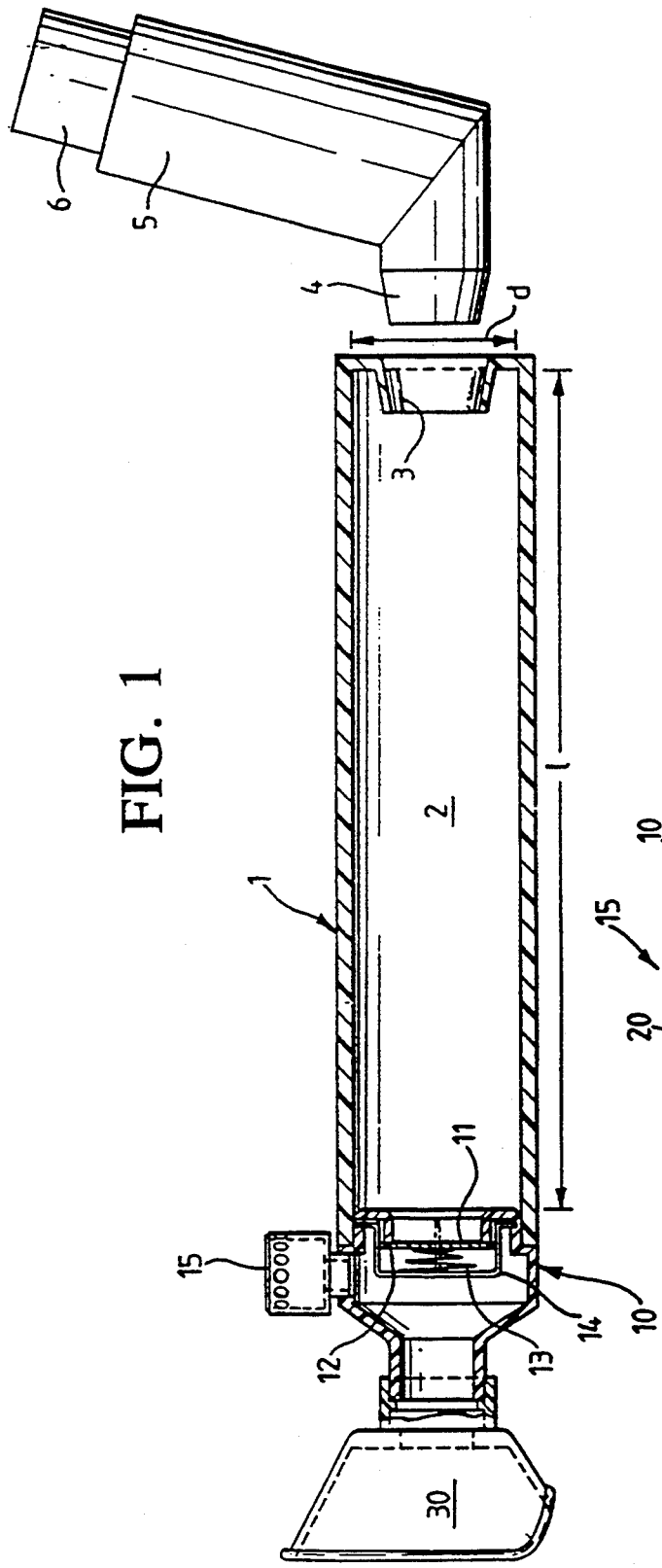
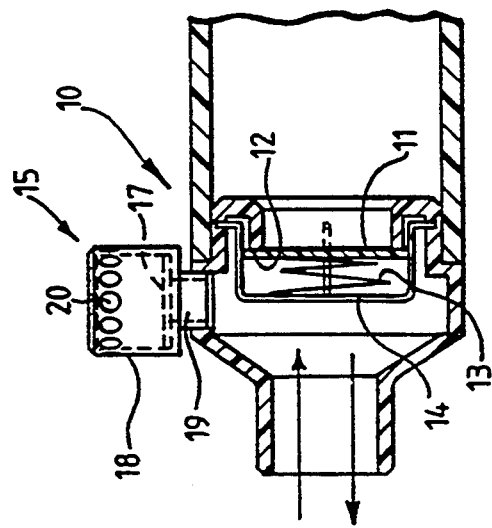

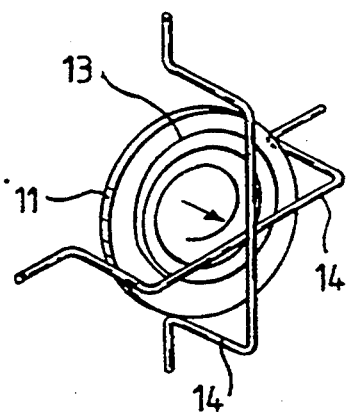
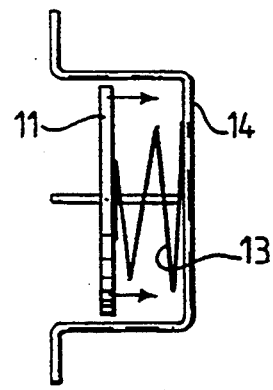
FIG. 3    FIG. 4
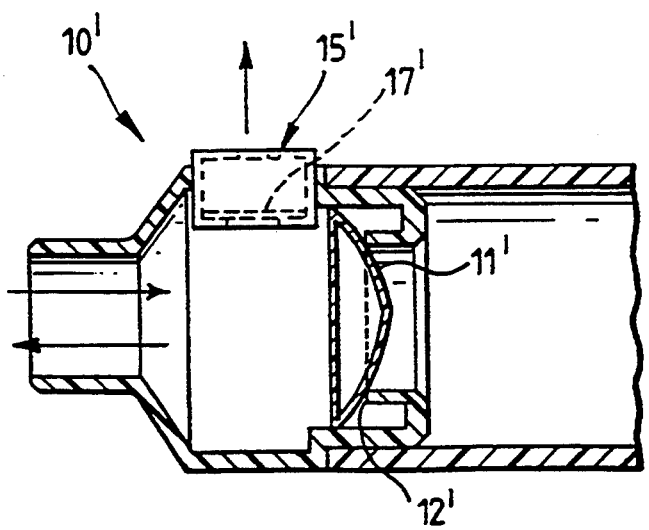
FIG. 5

VALVED AUXILIARY DEVICE FOR USE WITH AEROSOL CONTAINER

This is a continuation, of application Ser. No. 07/995,337, filed 22 Dec. 1992, which, in turn, was a continuation of application Ser. No. 07/887,559, filed 18 May 1992, now abandoned; which, in turn, was a continuation of application Ser. No. 07/743,910, filed 12 Aug. 1991, now abandoned; which, in turn, was a continuation of application Ser. No. 07/655,732, filed 14 Feb. 1991, now abandoned; which, in turn, was a continuation of application Ser. No. 07/509,961, filed 16 Apr. 1990, now abandoned.

BACKGROUND OF THE INVENTION

This invention relates to an auxiliary device for use with a metered-dose aerosol container, either with or without an actuator. The aerosol container, with or without actuator, is referred to below as a metered-dose aerosol device. In particular, the invention relates to a spacer device to be attached to a metered-dose aerosol device for use in infants and young children to enable them to inhale medicaments such as, for example, bronchodilators and corticosteroids.

There are a substantial number of infants and young children generally termed "wheezy infants" who suffer from wheezy bronchitis, and other bronchopulmonary diseases such as respiratory distress syndrome due to post hyaline membrane disease and broncho-pulmonary dysplasia or neonatal pneumonia. These diseases if left untreated will in a significant number of cases develop into asthma. These conditions and other conditions such as cystic fibrosis will respond to treatment with for example, inhaled bronchodilators and corticosteroids provided there is a suitable device able to administer the medicaments so that they can reach the lungs of the infants and young children.

Administration of medicaments to infants and young children by inhalation is currently carried out using electric nebulisers but these devices have the disadvantage that they cannot be used with infants at home or the medicaments have to be administered over a time consuming period for example up to 10 minutes making it difficult to obtain the cooperation of the infant. It can be appreciated that if treatment is to continue for example, 3 or 4 times a day, this can be inconvenient. There is also considerable loss of medicament with this method of administration.

Existing large volume spacers, typically having a volume of about 750 ml, which are on the market when used for infants and young children have the disadvantage that the volume is too large for the infants' lungs and the inlet valve has too high a resistance and does not work in a vertical position for use in infants.

It has been proposed to provide a spacer device for use by infants and young children. However, only one such device is commercially available anywhere. This device uses a chamber having a volume of about 140 ml which is adapted at one end to receive the outlet of a metered-dose inhaler. The chamber is 110 mm long, and at its other end it communicates via an inhalation valve, which is in the form of a slit membrane, with a mask intended to be placed over the nose and mouth of an infant or young child.

This device, however, has several disadvantages, the appreciation of which forms part of the present invention. Thus, it has been found that the inlet valve does not open sufficiently to enable the infants to inhale sufficient medicament. Also, a disadvantage has been appreciated in that because there is no separate exhalation valve the exhaled air can only be released by leakage around the edge of the mask.

SUMMARY OF THE INVENTION

The device of the present invention has been specially tailored for infants and young children and aims to avoid or at least mitigate some or all of the above mentioned disadvantages.

According to the present invention there is provided an auxiliary device for use with a metered-dose aerosol device, the auxiliary device comprising means defining a chamber having an inlet adapted to receive the metered-dose aerosol device, and an outlet; administration means adapted to communicate with the nose and/or mouth of an infant or young child and communicating with the chamber outlet via a first valve which permits the infant or young child to inhale aerosol-carrying air from the chamber, and communicating with atmosphere via a second valve permitting exhalation therethrough; the distance between the chamber inlet and the chamber outlet being such that the mass percentage of aerosol particles having a diameter of from 1.0 microns to 5.0 microns is substantially a maximum at the chamber outlet, and the volume of the chamber being from 200–500 ml.

The administration means is preferably an inhalation mask adapted to be positioned over the nose and mouth of the infant or young child, and for practical purposes a mask is essential when the infant is under 2 years of age, or of a size which one would expect in an infant under 2 years of age.

The ensuing description will refer simply to use by an infant. It is to be understood, however, that use by a young child, too old properly to be called an infant, is also covered by the present invention. By "infant or young child" we mean those up to and including 4 years of age, or of a size which one would expect in an infant or young child up to and including that age.

BRIEF DESCRIPTION OF THE DRAWINGS

FIG. 1 is a diagrammatic side elevation of an embodiment of a device according to the present invention with a metered-dose aerosol device shown adjacent thereto;

FIG. 2 shows in more detail, and on a larger scale, the arrangement of valves used in the embodiment of FIG. 1;

FIG. 3 shows a detail of the valve of FIG. 2;

FIG. 4 is a side elevational view of the valve shown in FIG. 3, with portions removed for clarity; and FIG. 5 shows a modified valve arrangement which may be used in place of that shown in FIGS. 1 to 4.

DESCRIPTION OF PREFERRED EMBODIMENTS

The embodiment of FIG. 1 comprises an elongate tube 1 of cylindrical cross-section. The: tube may conveniently be made of a transparent plastics material, such as an acrylic material. The transparency of the material allows the adult supervising the child to observe that the inhalation valve (see below) is working correctly. The tube 1 defines a chamber 2 having a volume of from 200 to 500 ml, preferably from 250–350 ml. A particularly preferred volume for use with one of the aerosol containers with which the invention may be used, namely Ventolin (salbutamol) is 350 ml, and details of this are given below. The distance down the tube from where the spray leaves the aerosol container (see below) to the downstream end of the tube is indicated in FIG. 1 by l and the internal diameter of the tube by d. Since, with the aerosol container in position, the point where the spray leaves it is substantially at the upstream end of the tube, the distance l is substantially the length of the chamber, and it is so referred to below and shown in FIG. 1 of the drawings. The significance of the volume and length of the chamber are discussed in more detail below.

The chamber is provided at its inlet end with walls 3 which are directed longitudinally inward and which are adapted to grip an outlet spout 4 of an actuator 5 inserted therein. The actuator receives a metered-dose aerosol container 6 therein which is adapted, when depressed, to dispense a metered dose of a medicament-containing aerosol through the outlet spout 4. The aerosol container 6 may be a can of known type and the actuator 5 may also be of known type, and the details of both are not relevant for the purposes of the present description, except that, as explained further below, the dimensions of the chamber 2 depend on the choice of aerosol actuator and aerosol container. Typically, the pressure within the aerosol may be from 40–110 psi (276–758 kPa), for example from 50–60 psi (345–414 kPa), the pressure being measured at 20°–25° C.

At its outlet end, the chamber is provided with a valve 10 which is adapted to open when the infant inhales and which is therefore referred to below as the inhalation valve. The valve 10 comprises a disk 11 which is biased into a closed position in which it bears against an annular seat 12 by means of a spring 13. The spring is trapped between the disk 11 and a pair of cross-wires 14 (see especially FIG. 3). Various alternative types of inhalation valve may be used, for example a cone-diaphragm valve (see FIG. 4).

The inhalation valve should be so constructed as to open once the pressure on the outlet side is less than that on the inlet side by a low value, preferably not more than about 0.03 kPa. The flow resistance of the valve should also be low, preferably not more than about 0.02 kPa/l/s for a flow rate of 75 ml/s.

The device is provided with a further valve 15 which opens when the infant exhales and closes during inhalation, and which is referred to herein as the exhalation valve. The valve 15 comprises a disk 17 trapped within a cylindrical chamber 18. It is advantageous for the chamber 18 to be made of a transparent or translucent material so that it can be seen that the valve is working correctly. During inhalation the reduced pressure on the lower side of the disk causes it to close a passageway 19 by which it is connected to the interior of the device, and thus to prevent air being inhaled through the passageway. During exhalation, when the valve 10 is closed, the increased pressure in the passageway 19 causes the disk 17 to rise and permits the air exhaled by the infant to pass through the passageway 19 and thence out through an array of apertures 20. The flow resistance of the exhalation valve should be sufficiently low that the positive end-expiratory pressure created thereby does not exceed about 0.05 kPa.

It is desirable that the dead space within the valve arrangement should be as small as possible, i.e. the space in the volume defined between the valves 10 and 15 and the region where the mask is attached, and in an actual example this was 16 ml.

The fact that an exhalation valve is provided in addition to an inhalation valve, unlike the known commercially available device referred to above which has an inhalation valve only, provides a significant benefit. The known device relies on leakage around the edge of the mask to permit passage of exhaled air, and if this is insufficient an attendant, for example a parent of the infant, must alternately withdraw the mask from the face and replace it, in unison with the breathing of the infant.

To permit use by an infant a mask 30 is provided which is of a suitable size and shape to cover the nose and mouth of the infant.

The device is conveniently made in three detachable units, to facilitate manufacture and cleaning. The tube 1, including the walls 3, constitutes one unit. The mask 30 constitutes a second unit. The remainder of the device, i.e. the portion which carries the valves 10 and 15, constitutes a third unit. The fact that the mask is removable means that as the child grows the mask can be removed and replaced with a larger sized mask.

Reference has been made above to the significance of the dimensions of the chamber 2, and this will now be explained further.

Firstly, the volume of the chamber is important. The tidal volume of inhalation of an infant is normally 5–8 ml/kg body weight. However, infants in respiratory distress have a tidal volume approximately equal to from 7–14 ml/kg body weight. The volume of the chamber should be substantially greater than the tidal volume of the user, and should preferably be from 5 to 15 times the tidal volume, more preferably 5 to 10 times.

It has been found in an investigation of the breathing of twenty infants with brocho-pulmonary disease that, on average, even during respiratory distress, they took from 4 to 11 breaths (mean value 7.0±2.2) every 10 seconds. The infants investigated were aged from 0.8 to 18.8 months and had weights of from 2.86 to 12.3 kg. Over a period of 10 seconds, the total volume inspired exceeded 350 ml in the case of 80% of the infants, and in no case did the volume fall below 200 ml.

Secondly, the length of the chamber is important. In an aerosol, the aerosol particles cover a range of sizes and it has been found that the size distribution varies with the distance from the valve orifice of the aerosol container. The size of particles inhaled by the user should, as far as possible, lie between 1.0 microns and 5.0 microns. Particles smaller than 1 micron in diameter tend to be exhaled. Particles greater than 5 microns in diameter tend to be deposited before reaching the lungs.

It has been found that the distance from the valve orifice at which the mass percentage of particles in the desired size range is at a maximum varies from case to case, though in all those studied so far the optimum distance is significantly greater than the distance of 110 mm present in the commercially available device referred to above. Tests have been carried out on three bronchodilator metered dose inhaler suspension aerosols, namely Ventolin (salbutamol), Berotec (fenoterol) and Bricanyl (terbutaline), (Ventolin, Berotec and Bricanyl are Trade Marks). These tests showed that the maximum mass percentage of particles between 0.5 microns and 5 microns was achieved at 230 mm for Ventolin (54%), at 130 mm for Berotec (45%) and at 280 mm for Bricanyl (56%).

In a particular spacer device of the type shown in FIG. 1, intended for use with Ventolin in an aerosol container at a pressure of about 50 psi (345 kPa), l was 230 mm and d was 44 mm. Consequently, the volume of the chamber was 350 ml.

It is believed that the optimum distance, depends, inter alia, on the pressure within the aerosol container, the design of metering valve used in the aerosol container and the design of the nozzle of the aerosol dispenser. For any particular case the optimum distance can be determined by routine experimentation. In addition to the medicaments referred to above, the device of the present invention can, of course, also be used for other medicaments which are to be inhaled, for example those sold under the trade marks Becotide, Becloforte and Yentide.

In the modified valve 10' shown in FIG. 4, the components which correspond generally to components shown in FIGS. 1 to 3 are denoted by the same reference numeral but with the addition of a prime. It will be seen that the valve 15' is located inwardly compared to the valve 15, so as to reduce the risk of its being damaged in use. The disk 11 is replaced by a cone-type diaphragm valve 11'.

Various other modifications may be made to the device described. For example, the illustrated tube 1 may be replaced by a tube which consists of a plurality of telescopically arranged sections, whereby the length l can be varied according to the nature of the aerosol container and actuator being used.

What is claimed is:

1. An auxiliary device for use with a metered-dose aerosol device, the auxiliary device comprising means for defining a chamber, a chamber inlet communicating with said chamber and adapted to receive the metered-dose aerosol device, and a chamber outlet communicating with said chamber; a first valve and a second valve; administration means adapted to communicate with the nose and/or mouth of an infant or young child and communicating with said chamber outlet via said first valve which permits the infant or young child to inhale aerosol-carrying air from the chamber, and communicating with atmosphere via said second valve permitting exhalation therethrough; the distance between said chamber inlet and said chamber outlet being such that the mass percentage of aerosol particles having a diameter of from 1.0 microns to 5.0 microns is substantially a maximum at said chamber outlet and the chamber defining a fixed volume of from 250–350 ml, wherein the chamber is substantially cylindrical, and said administration means comprising an inhalation mask adapted to be positioned over the nose and mouth of the infant and young child.

2. An auxiliary device according to claim 1, wherein the mask is removable from the remainder of the device.

3. An auxiliary device according claim 1, wherein the volume of the chamber is substantially 350 ml.

4. An auxiliary device according to claim 1, wherein the length of the chamber is substantially 230 mm.

5. An auxiliary device according to claim 1, wherein the chamber inlet is adapted to receive an outlet spout of an aerosol actuator which is itself adapted to receive an aerosol container.

6. An auxiliary device according to claim 1, wherein said first valve has an inlet and an outlet, said first valve opening when the pressure difference between its inlet and outlet reaches a predetermined value which is not more than 0.03 kPa.

7. An auxiliary device according to claim 1, wherein said first valve having a flow resistance not greater than 0.02 kPa/l/s for a flow rate of 75 ml/s.

8. An auxiliary device for use with a metered-dose aerosol device, the auxiliary device comprising chamber means for defining a chamber, a chamber inlet communicating with said chamber for receiving the metered-dose aerosol device, and a chamber outlet communicating with said chamber; a first valve and a second valve; administration means adapted to communicate with the nose and/or mouth of an infant or young child and communicating with said chamber outlet via said first valve which permits the infant or young child to inhale aerosol-carrying air from the chamber, and communicating with atmosphere via said second valve permitting exhalation therethrough; the distance between said chamber inlet and said chamber outlet being such that the mass percentage of aerosol particles having a diameter from 1.0 microns to 5.0 microns is substantially a maximum at said chamber outlet, and the chamber defining a fixed volume of from 200–500 ml.; said administration means comprising an inhalation mask adapted to be positioned over the nose and/or mouth of the infant or young child, said first valve having an inlet and an outlet, said first valve opening when the pressure difference between its inlet and outlet reaches a predetermined value which is not more than 0.03 kPa, and the flow resistance of said first valve is not greater than 0.02 kPa/l/s for a flow rate of 75 ml/s.

* * * * *